US012629484B2

(12) United States Patent (10) Patent No.: US 12,629,484 B2
Bartels et al. (45) Date of Patent: May 19, 2026

(54) HIGH PRESSURE INHALATION DEVICE

(71) Applicant: INVOX BELGIUM NV, Diepenbeek (BE)

(72) Inventors: Frank Bartels, Hattingen (DE); Juergen Rawert, Cologne (DE)

( * ) Notice: Subject to any disclaimer, the term of this patent is extended or adjusted under 35 U.S.C. 154(b) by 724 days.

(21) Appl. No.: 17/266,121

(22) PCT Filed: Aug. 7, 2019

(86) PCT No.: PCT/EP2019/071195
§ 371 (c)(1),
(2) Date: Feb. 5, 2021

(87) PCT Pub. No.: WO2020/030682
PCT Pub. Date: Feb. 13, 2020

(65) Prior Publication Data
US 2021/0290863 A1 Sep. 23, 2021

Related U.S. Application Data

(60) Provisional application No. 62/717,614, filed on Aug. 10, 2018.

(30) Foreign Application Priority Data

Aug. 10, 2018 (EP) ..................................... 18188584

(51) Int. Cl.
*A61M 11/00* (2006.01)
(52) U.S. Cl.
CPC ................................. *A61M 11/007* (2014.02)
(58) Field of Classification Search
CPC .............. A61M 11/001; A61M 11/007; A61M 15/0065; A61M 16/208; A61M 2205/071;
(Continued)

(56) References Cited

U.S. PATENT DOCUMENTS 4,603,794 A * 8/1986 DeFord ............... B05B 11/1015
239/327
6,398,074 B1 * 6/2002 Bruna ............... A61M 15/0028
222/386
(Continued)

FOREIGN PATENT DOCUMENTS

CA 2653422 A1 12/2007
CN 1199009 A 11/1998
(Continued)

OTHER PUBLICATIONS

International Preliminary Report on Patentability and Written Opinion of the International Searching Authority for PCT/EP2019/071195, Feb. 16, 2021, 7 pages.

*Primary Examiner* — Justine R Yu
*Assistant Examiner* — Matthew D Ziegler
(74) *Attorney, Agent, or Firm* — Synergy IP AG

(57) ABSTRACT

An inhalation device for providing a particularly high pressure for nebulization. The inhalation device can include a housing, a reservoir, a pumping unit adapted to receive the delivery of mechanical energy to the pumping unit, and a nozzle. The pumping unit can also include a hollow cylindrical part and a piston, the cylindrical part having an interior space with a defined first cross section configured to receive an upstream end portion of the piston, wherein the cylindrical part and the piston are linearly moveable relative to one another such as to form a pumping chamber having a variable volume.

18 Claims, 2 Drawing Sheets

(58) Field of Classification Search
CPC ...... A61M 2205/3331; A61M 2205/58; A61M
2205/8218; A61M 2206/16
See application file for complete search history.

(56) References Cited

U.S. PATENT DOCUMENTS

| | | | | |
|---|---|---|---|---|
| 8,550,300 B2 * | 10/2013 | Lee | ................... | B05B 11/00444 |
| | | | | 222/105 |
| 9,050,428 B2 * | 6/2015 | Dunne | ................... | B65D 83/62 |
| 9,550,025 B2 * | 1/2017 | Dunne | ............... | A61M 5/2033 |
| 9,964,100 B2 | 5/2018 | Vogt | | |
| 2003/0209238 A1 | 11/2003 | Peters et al. | | |
| 2004/0068222 A1 | 4/2004 | Brian | | |
| 2009/0114215 A1 | 5/2009 | Boeck et al. | | |
| 2012/0132199 A1 * | 5/2012 | Kiesewetter | ......... | A61M 11/007 |
| | | | | 128/200.22 |
| 2012/0167878 A1 * | 7/2012 | Belson | ................... | A61M 16/12 |
| | | | | 128/200.14 |
| 2015/0238710 A1 | 8/2015 | Vogt | | |

FOREIGN PATENT DOCUMENTS

| | | | |
|---|---|---|---|
| CN | 104863639 | A | 8/2015 |
| EP | 0627230 | B1 | 2/2000 |
| JP | S59158460 | A | 7/1984 |
| JP | 5509241 | A | 12/1993 |
| JP | 2009538656 | A | 11/2009 |
| JP | 2012517831 | A | 8/2012 |
| JP | 2015226761 | A | 12/2015 |
| RU | 2495726 | C2 | 10/2013 |
| WO | 1991014468 | | 10/1991 |
| WO | 2018197730 | A1 | 11/2018 |

* cited by examiner

HIGH PRESSURE INHALATION DEVICE

CROSS REFERENCE TO RELATED APPLICATIONS

This application is a United States National Stage Application filed under 35 U.S.C. § 371 claiming the benefit of PCT Application No. PCT/EP2019/071195, filed on Aug. 7, 2019, which claims priority to and the benefit of European Application No. 18188584.9, filed on Aug. 10, 2018, and U.S. Provisional Application Ser. No. 62/717,614, filed on Aug. 10, 2018, all of which are incorporated herein by reference in their entireties.

FIELD OF THE INVENTION

The invention relates to the field of inhalation devices for medically active liquids. In particular, the invention relates to an inhalation device providing a particularly high pressure for nebulization.

BACKGROUND OF THE INVENTION

Nebulizers or other aerosol generators for liquids are known from the art since a long time ago. Amongst others, such devices are used in medical science and therapy. There, they serve as inhalation devices for the application of active ingredients in the form of aerosols, i.e. small liquid droplets embedded in a gas. Such an inhalation device is known e.g. from document EP 0 627 230 B1. Essential components of this inhalation device are a reservoir in which the liquid that is to be aerosolized is contained; a pumping unit for generation of a pressure being sufficiently high for nebulizing; as well as an atomizing device in the form of a nozzle.

An improvement of such an inhalation device is disclosed in patent application PCT/EP2018/061056, filed by the same applicant as the present invention, the content of which is incorporated herein in its entirety.

Depending on the specific application, the amount of nebulized liquid per single dose is, with currently available soft mist inhalation devices, typically in the range of about 15 μl, whereas the delivery of higher volumes of up to 250 μl per dose would be desirable. Even conventional propellant-driven metered-dose inhalers are only suitable for delivering single doses up to 50-80 μl per actuation. One potential solution is to simply repeat a dosing cycle for one or more times, such that one single dose is delivered with two or more consecutive device actuations. However, this results in a longer emission time, which is further increased by that fact that the time for re-filling of the device's pumping chamber must be added as well. Also, the repeated and reproducible activation of a device by a user might be problematic; in particular with respect to active components that must unfold their effect immediately such as asthma medicaments or the like.

OBJECT OF THE INVENTION

The object of the invention is the provision of a device that avoids the drawbacks of the known art. The device shall allow to emit high volume amounts of a medically active liquid in a sufficiently short time with only a single dosing cycle.

SUMMARY OF THE INVENTION

In a first aspect, the present invention provides an inhalation device for generation of an aerosol of a medically active liquid, comprising:

a housing (1), inside this housing (1) a reservoir (2) for storing said medically active liquid, downstream this reservoir (2) a pumping unit (3) for generation of a pressure connected to a means for the delivery of mechanical energy (4) to said pumping unit (3), and downstream said pumping unit (3) a nozzle (5); wherein the pumping unit (3) comprises a hollow cylindrical part (3A) and a piston (3B), the cylindrical part (3A) having an interior space (3C) with a defined first cross section (A1) configured to receive an upstream end portion (3B') of said piston (3B), wherein said cylindrical part (3A) and said piston (3B) are linearly moveable relative to one another such as to form a pumping chamber having a variable volume, wherein the means for the delivery of mechanical energy (4) is a pressurised gas, wherein the inhalation device comprises a pressure chamber (6) having an internal volume for holding said pressurized gas, a wall of said pressure chamber (6) being provided by a plunger (7) which is configured to perform a reciprocating linear movement such as to change the internal volume of the pressure chamber (6), wherein the plunger (7) is mechanically coupled to the piston (3B) or to the cylindrical part (3A) of the pumping unit (3), and wherein the plunger (7) exhibits a cross section (A2) which is larger than the cross section (A1) of the pumping chamber.

In a second aspect, the invention provides a method for generation of an aerosol of a liquid by means of an inhalation device according to the first aspect of the invention, wherein the method comprises the following steps:

in a filling phase, providing a negative gauge pressure inside the pumping chamber by increasing its volume, and thereby filling the pumping chamber with liquid from the reservoir (2) due to said negative gauge pressure;

in an emission phase, providing a positive gauge pressure inside the pressure chamber (6) having said second cross section (A2), and thereby effecting a movement of the plunger (7);

transferring said movement mechanically to the piston (3B) or to the cylindrical part (3A), such that the volume of the pumping chamber is reduced, and a positive pressure is generated inside its interior space; and thus emitting the medically active liquid from the pumping chamber through the nozzle (5);

wherein the pressure of the pressure chamber (6) is amplified.

DESCRIPTION OF THE INVENTION

The object is solved by an inhalation device for generation of an aerosol of a medically active liquid, comprising:

a housing (1), inside this housing (1) a reservoir (2) for storing said medically active liquid, downstream this reservoir (2) a pumping unit (3) for generation of a pressure connected to a means for the delivery of mechanical energy (4) to said pumping unit (3), and downstream said pumping unit (3) a nozzle (5); wherein the pumping unit (3) comprises a hollow cylindrical part (3A) and a piston (3B), the cylindrical part (3A) having an interior space (3C) with a defined first cross section (A1) configured to receive an upstream end portion (3B') of said piston (3B), wherein said cylindrical part (3A) and said piston (3B) are linearly moveable relative to one another such as to form a pumping chamber having a variable volume, wherein the means for the delivery of mechanical energy (4) is a pressurised gas, wherein the inhalation device comprises a pressure chamber (6) having an internal volume for holding said pressurized gas, a wall of said pressure chamber (6) being provided by a plunger (7) which is configured to perform a reciprocating linear movement such as to change the internal volume of the pressure chamber (6), wherein the plunger (7) is mechanically coupled to the piston (3B) or to the cylindrical part (3A) of the pumping unit (3), and wherein the plunger (7) exhibits a cross section (A2) which is larger than the cross section (A1) of the pumping chamber.

Advantageous embodiments are described in the respective dependent claims, the subsequent description, as well as the accompanying figures.

The inhalation device is suitable for the generation of an aerosol from medically active liquids for inhalation therapy. In particular, the inhalation device is adapted for the dose-wise generation and emission of nebulized aerosols suitable for the pulmonary delivery of medically active ingredients. The term medically active liquids as used herein also includes medically active fluids.

Typically, such an inhalation device comprises a housing, inside this housing a reservoir for storing a liquid, such as a medically active liquid. The reservoir may have a capacity for storing e.g. a liquid volume of about 1 to about 50 ml or from about 5 ml to about 15 ml. Downstream of this reservoir, the device comprises a pumping unit which is preferably based on the principle of a piston pump or plunger pump, and downstream said pumping unit a nozzle. Obviously, the pumping unit is fluidically connected to both the nozzle and the reservoir.

The pumping unit which serves for generation of a pressure is connected to, or driven by, a means for the delivery of mechanical energy to said pumping unit. By said means, the pumping unit is supplied with a predefined, relatively constant peak amount of mechanical energy which is sufficient for generating the required emission pressure which typically ranges from about 30 bar to about 300 bar as described in further detail below. As a result, the emission or delivery performance of the device is exceptionally reproducible, compared with devices where the emission pressure is provided manually by the user, and thus, varies substantially during the emission phase.

More specifically, said pumping unit comprises a hollow cylindrical part having an interior space, typically with a volume within the range of from about 1 μl to about 500 μl, or from about 5 μl to about 250 μl. It is noted that the term "cylindrical part" refers to a part having a cylindrical internal surface; the outside as well as a portion which does not come in contact with the riser pipe and/or the seal do not have to be cylindrical.

The pumping unit further comprises a piston. The interior space of the cylindrical part has a defined cross section (subsequently also referred to as "first" cross section) and is configured to receive an upstream end portion of said piston. It is clear that the cross section of the piston must substantially match the cross section of said interior space. In case that the interior space has in fact a wider cross section, only that portion of the cross section is used for the present definition of "first cross section" that matches the piston's cross section. Thus, alternatively, the piston's cross section could also be used to further describe the present invention.

Further, said cylindrical part and said piston are linearly moveable relative to one another such as to form a pumping chamber having a variable volume. Thus, by altering the volume, the pressure inside said pumping chamber is altered accordingly.

According to the invention, the aforesaid means for the delivery of mechanical energy is a pressurised gas.

Known devices, amongst others, make use of elastic springs as means for the delivery of mechanical energy which are manually loaded prior to the emission phase. While said springs have the advantage of providing, in principle, an unlimited number of dosing cycles, the amount of mechanical energy which can be stored with such a spring for a single cycle, and thus, which is supplied during the emission phase, is limited, as is the obtainable pressure inside the pumping chamber and therefore, the dosing volume and time.

In contrast, the present invention makes use of a means that can provide a much higher pumping pressure. Depending on the concrete embodiment, said pressure can also be supplied for a longer time within a pumping cycle, thus enabling a higher dosing volume per cycle.

Further, the device comprises a "pressure chamber" (not to be confused with the aforesaid pumping chamber). This pressure chamber has an internal volume for holding said pressurized gas. One wall of said pressure chamber is provided by a moveable plunger which is configured to perform a reciprocating linear movement such as to change the internal volume of the pressure chamber. In other words, the plunger is driven by the increase (or decrease) of pressure within the pressure chamber, which is containing a pressurized gas. The higher the pressure is, the larger is the force that acts onto the plunger.

Further, the plunger is mechanically coupled to the piston or to the cylindrical part (depending on which of these components of the pumping unit is moveable). As a result, a movement of the plunger results in a movement of the piston or the cylindrical part. In other words, the plunger "drives" the piston or cylindrical part and thus, can effect a change of volume (and thus, of pressure) inside the pumping chamber.

To achieve an amplification of pressure, the plunger exhibits a (second) cross section which is larger than the (first) cross section of the pumping chamber to which it is mechanically coupled. In this way, a "pneumatic lever" mechanism is provided which makes use of the fact that the force is proportional to the product of pressure and area. Since the areas, namely the first and (larger) second cross section, are different, a first pressure (inside the pressure chamber) is translated into a second (and higher) pressure inside the pumping chamber. Said pressure can advantageously be used for high emission rates and/or short emission times.

Preferably, the ratio of second to first cross section is greater than 2, or greater than 5, and preferably even greater than 10, such as within a range of from about 10 to about 500. As a result, the pressure can as well be increased by a factor of 10 or higher, such as from about 10 to about 100. If e.g. the means for the delivery of mechanical energy provides a pressurised gas having a pressure of 10 bar, a pressure of 100 bar can be obtained in the pumping chamber of the pumping unit, which is particularly advantageous as such high pressure enables long aerosol emission phases, high emission rates and thereby high liquid volumes that can be delivered per pumping cycle. Another potential advantage is that liquids with higher viscosities than typical aqueous formulations may be aerosolized, such as liquids with a viscosity in the range of from about 1 to about 100 mPa·s (cP). Moreover, the invention is particularly suitable for inhalation devices which exhibit nozzles requiring a high working pressure, such as impingement-type nozzles. By means of the invention, depending on the viscosity of the liquid and the nozzle type, within a time of 1.5 to 2.0 seconds, a volume typically within the range of from about 1 μl to about 500 μl, or from about 5 μl to about 250 μl, for example of about 50 μl can be nebulized.

According to one embodiment, the pressurised gas is provided by a container filled with pressurized and/or liquefied gas. Preferably, the container contains liquefied gas; as is commonly known, a container which comprises some liquefied gas (without being entirely filled by the liquefied gas) will also contain some pressurized gaseous (non-liquid) gas which is at equilibrium with the liquid gas. Examples of potentially useful liquefied gases include liquefied propane, n-butane, isobutane, nitrous oxide, carbon dioxide, dimethyl ether, methyl ethyl ether, hexafluoroacetone, hydrofluoroalkanes (such as HFA 134a or HFA 227), or any mixtures thereof. Among the preferred liquefied gases to be used according to the invention are liquefied propane, propane/butane mixtures and/or nitrous oxide.

Preferably, the container is part of a preferably exchangeable cartridge, so that, when the remaining pressure inside the container falls below a minimum threshold, the container can be removed from the housing of the inhalation device, and a fresh cartridge can be inserted. With one cartridge, a number of e.g. 50 to 200 cycles can be reached without any problems.

According to another embodiment, the pressurised gas is provided by a chamber which is manually pressurizable, and which can temporarily hold and controllably release said pressurised gas. This means that the pressure within the pressure chamber can be increased manually, e.g. by repeatedly actuating a pump or the like. Such a pump can be actuated by a linear as well as a rotating motion and is preferably a part of the inhalation device. The inhalation device can comprise a means for monitoring the pressure, and/or for notification that a sufficient amount of pressure is present for using the device. After reaching the required pressure, the device is ready to use. Since the manual loading of the pressure chamber is performed prior to the actual dosing, the latter is not interrupted as it is the case with devices known in the art which make use of a series of dosing strokes.

While the embodiment using a container or cartridge with liquefied gas provides a particularly comfortable user experience, the latter embodiment, i.e. an embodiment using on-demand manually pressurizable gas, is very flexible as it is potentially independent of the necessity of refilling, except with regard to the liquid to be aerosolized, e.g. the medically active liquid. Also, the fact that a device according to the latter embodiment does, in the inactivated state, not contain any pressurised components, may be advantageous in that less regulatory requirements apply which must be complied with.

According to one embodiment, the piston is hollow. The hollow space can serve as a means for fluidically connecting the pumping chamber with the nozzle(s), or with the reservoir. For this, the downstream end of the piston can directly or indirectly be fluidically connected with said nozzle, or the upstream end of the piston may be provided with a direct or indirect fluid connection to the reservoir.

In another embodiment, the piston is solid. In this case, other measures must be taken in order to provide an outlet from the pumping chamber. This can e.g. be achieved by providing one or more openings in the side walls of the pumping chamber that are not covered at any stage of the pumping cycle by the upstream end of the piston, e.g. at a position close to the inlet which is connected with the reservoir. Said opening(s) is (are) then connected with the nozzle(s).

According to one embodiment, the piston is immobile and firmly attached to the housing or to the nozzle, and the hollow cylindrical part is moveable relative to the housing or to the nozzle. This embodiment could be called a "moving chamber" embodiment, since the major part of the chamber including the side wall are mobile. The movement of the hollow cylindrical part is driven by the mechanically coupled plunger.

According to another embodiment, the hollow cylindrical part is immobile and firmly attached to the housing or to the nozzle, and the piston is moveable relative to the housing or to the nozzle. Accordingly, this embodiment could be called a "moving piston" embodiment. The movement of said piston is driven by the mechanically coupled plunger.

According to another embodiment, the cylindrical part as well as the piston are moveable. A relative movement of both parts with respect to each other still results in the desired volume change of the pumping chamber. Both parts can be moveable in parallel or anti-parallel direction upon a propulsive movement of the plunger.

In one embodiment, a check valve is arranged upstream the pumping chamber in order to "actively" block backflow of liquid in direction of the reservoir. Presently, the term "actively" indicates that a dedicated component is provided to avoid said backflow. In contrast, a "passive" means is a means that functions simply due to its dimensions, such as a particularly narrow tube, or a specifically shaped outlet opening towards the nozzle. In any case, measures should be taken in order to at least reduce said backflow.

In one embodiment, in addition to the aforementioned "direct" pneumatic/hydraulic coupling that makes use of differently sized areas that are subjected to pressures, a mechanical lever mechanism is provided for further increasing the amplification effect of the aforesaid ratio. In other words, by additionally providing a mechanical lever or the like which transfers e.g. a long, but weaker stroke into a short, but stronger stroke, the amplification can further be increased. Such a lever can be constructed as e.g. a two-arm lever, or make use of a cam mechanism that uses an inclined surface as the lever means.

In another embodiment, a means for the temporary storage of mechanical energy is provided which is loadable by a propulsive movement of the plunger, and which is configured, by unloading its stored energy, to effect a retropulsive movement of the plunger.

In other words, said means, which must not be confused with the above-mentioned means for the delivery of mechanical energy which effects an increase of pressure in the pumping chamber, serves for generating a vacuum, or negative gauge pressure, inside the pumping chamber so that it is refilled with liquid from the reservoir. This is achieved in that said means is, during the emission phase, loaded with an amount of mechanical energy which is, during the refilling phase, sufficient to "push away" the cylindrical part from the piston or vice versa and thus enlarge the interior space of the pumping chamber. This amount of energy is significantly lower than the amount which is provided by the means for the delivery of mechanical energy; therefore, the energy available for the dosing is only insignificantly reduced by the loading of the means for the temporary storage of mechanical energy.

In this way, the means for the temporary storage of mechanical energy serves as a means for resetting the volume of the pumping chamber.

Preferably, said means for the temporary storage of mechanical energy is an elastic spring, a gas spring, or a magnetic spring. The spring is arranged in that it rests against an inside wall of the housing with one end, and against the moveable part (piston or cylindrical part) with the other. By compressing the spring during the emission phase, the energy is stored; it is released again when the spring relaxes while resetting the volume of the pumping chamber.

It is clear that, if an extension spring or other is used, the construction must be adapted accordingly.

In one of the preferred embodiments, the nozzle of the inhalation device is selected from the nozzle types which exhibit, or require, a high operational pressure for atomizing a liquid. For example, the nozzle may require a pressure of 30 bar or higher, such as from 30 to 300 bar; or of 50 bar or higher, such as from 50 to 300 bar; or of 100 bar or higher, such as from 100 to 300 bar, respectively.

In one of the particularly advantageous embodiments, the nozzle is of the impingement type. Such nozzles are well known and provide, by collision of two or more colliding jets of liquid, a fine and sufficiently homogenous atomisation into droplets which can be inhaled by the user. The nozzle can also provide more than one layer with nozzle exits, or more than one pair of nozzle exits in one layer in order to further increase the amount of liquid that can be atomized in one cycle.

According to another embodiment, the nozzle is of the Raleigh or swirl type.

In another embodiment, the volume of the pumping chamber amounts to at least 15 µl, or at least 30 µl, or at least 50 µl, or about 100 µl to 250 µl, respectively.

In yet another embodiment, the pumping unit is configured to provide a peak pressure of at least 30 bar, and preferably at least 100 bar, and most preferably at least 200 bar inside the pumping chamber. The means for the delivery of mechanical energy is configured to provide a pressure of at least 10 bar, and preferably at least 20 bar, and most preferably at least 50 bar inside the pressure chamber. As used herein, these (peak) pressure values refer to the maximum pressure in the pumping chamber during a pumping cycle.

Experiments have shown that amounts of this value are sufficient to provide a user with a sufficiently large amount of nebulised medically active liquid by only a single dosing cycle.

In a further preferred embodiment, the pumping chamber has an internal volume of at least about 50 µl, such as from about 50 µl to about 500 µl or to about 250 µl and is configured to provide a peak pressure of at least about 100 bar.

In one embodiment, (i) the plunger and (ii) the piston and/or the cylindrical part are moveable in parallel directions. Both component groups can be arranged next to each other, but they can also be aligned with each other, so that their respective moving directions are collinear.

In one embodiment, the pressure chamber is provided by two parallel plates, such as disks, that are capable of sliding inside the housing. If the distance between said plates is enlarged, the pressure chamber's volume increases and vice-versa. One of the plates may serve as the mechanical connection or "coupling" to the pumping unit. Thus, when the pressure chamber expands, said "coupling" plate preferably moves alone and in a direction that decreases the volume of the pumping chamber. In order to expel the gas which is accumulated inside the pressure after the emission phase, the coupling plate stays in place and the other "pressure" plate moves such that the volume of the pressure chamber is reduced (reset) again. In the refilling phase, both plates move in parallel, so that the volume of the pumping chamber is enlarged, while the volume of the pressure chamber remains constant.

The term 'medically active liquid' as used herein is to be understood in a broad sense and, in specific embodiments, means a liquid or liquid composition that may be useful for the treatment, stabilization or prevention of a condition, disorder or disease, specifically of a pulmonary condition, disorder or disease of an animal or human, preferably of a human.

In specific embodiments, a 'medically active liquid' may be a compound or a mixture of compounds per se. In other specific embodiments a medically active liquid may be a solution, suspension or dispersion of an ingredient or active ingredient in a physiologically acceptable carrier or liquid. In further specific embodiments, the physiologically acceptable carrier liquid may be water or an aqueous mixture comprising water and one or more further physiologically acceptable solvents such as ethanol, propylene glycol or polyethylene glycol.

In further specific embodiments, the medically active liquid my be an aqueous solution of a physiologically acceptable salt such as sodium chloride (saline). In a particular embodiment, the medically active liquid as used herein may be an aqueous solution of sodium chloride (saline) which may have a concentration of sodium chloride typically within the range of from about 0.5 wt.-% to about 15 wt.-%, or from about 0.9 wt.-% to about 10 wt.-% or from about 2 wt.-% to about 5 wt.-% or to about 4 wt.-% such as about 3.0 wt.-%, wherein the concentration refers to the weight of the final aqueous solution.

In specific embodiments, the term 'medically active liquid' as used herein may refer to a medically active liquid in form of a pharmaceutical composition comprising at least one active pharmaceutical ingredient (API), more specifically at least one inhalable active pharmaceutical ingredient.

More specifically, such at least one inhalable active pharmaceutical ingredient may, for example, be selected from long-acting muscarinic antagonists (LAMA), long-acting beta agonists (LABA) and inhalable glucocorticoids (ICS), as well as from analgetics and antidiabetics, either alone or in combination which each other.

Examples for long-acting muscarinic antagonists (LAMA) comprise, but are not limited to aclidinium bromide, glycopyrronium salts, such as glycopyrronium bromide, revefenacin, tiotropium, such as tiotropium bromide, umeclidinium bromide, oxitropium bromide, flutropium bromide, ipratropium bromide, trospium chloride, tolterodine.

Examples for long-acting beta agonists (LABA) comprise, but are not limited to, albuterol, arformoterol, bambuterol, bitolterol, broxaterol, carbuterol, clenbuterol, fenoterol, formoterol, hexoprenaline, ibuterol, indacaterol, indacterol, isoetharine, isoprenaline levosalbutamol, mabuterol meluadrine, metaproterenol, olodaterol, orciprenaline, pirbuterol, procaterol, reproterol, rimiterol, ritodrine, salmeterol, salmefamol, soterenot, sulphonterol, tiaramde, terbutaline, terbuterol.

Examples of inhalable glucocorticoids (ICS) comprise, but are not limited to, prednisolone, prednisone, butixocort propionate, flunisolide, beclomethasone, triamcinolone, budesonide, fluticasone, mometasone, ciclesonide, rofleponide, dexamethasone, etiprednol-dichloroacetat, deflazacort, etiprednol, loteprednol, RPR-106541, NS-126, ST-26.

Furthermore, active pharmaceutical ingredients may be selected from analgetics, such as opioid analgetics (e.g. morphine, fentanyl) or non-opioid analgetics (e.g. salicylic acid derivates, e.g. acetylsalicylic acid) or cannabinoids (e.g. tetrahydrocannabinol), antidiabetics, such as insulin.

The medically active liquid or liquid pharmaceutical composition that may be nebulized or aerosolized by the present inhalation device may comprise at least one active pharmaceutically ingredient as described above, but may also comprise a mixture of two or more active pharmaceutically ingredients that may be administered by inhalation.

The medically active liquid or pharmaceutical composition that may be aerosolized by the inhalation device according to the invention is preferably formulated as a composition that is suitable, and adapted for inhalative use, in other words a composition that may be nebulized or aerosolized for inhalation and that is physiologically acceptable for inhalation by a subject.

The medically active liquid or pharmaceutical composition that may be administered by the inhalation device according to this aspect of the invention or contained within the inhalation device and reservoir may be in the form of a dispersion, for example a suspension with a liquid continuous phase, and a solid dispersed phase or in the form of a solution.

In further embodiments, the medically active liquid or pharmaceutical composition as described above may comprise, optionally and in addition to the one or more active pharmaceutical ingredient, one or more physiologically acceptable excipients, which are suitable for inhalative use. Excipients which may be featured in the composition may include, but are not limited to, one or more buffering agents to regulate or control pH of the solution, salts, taste-masking agents, surfactants, lipids, antioxidants, and co-solvents, which may be used to enhance or improve solubility, for example ethanol, or a glycol.

In specific embodiments, the medically active liquid as described above may be essentially free of a propellant.

In further specific embodiments, the medically active liquid as described above may be an aqueous solution, in which one or more active pharmaceutical ingredients as described above are dissolved and solubilized in a liquid carrier solution comprising water. Such aqueous solutions optionally may also comprise one or more excipients as described above.

In a second aspect, the invention also relates to a method for generation of an aerosol of a medically active liquid by means of an inhalation device as defined above. In order to avoid repetitions, reference is made to the according explanations regarding such an inhalation device and its preferred embodiments and to medically active liquids and preferred embodiments.

The method comprises the following steps which form an entire dosing cycle:

In a filling phase, a negative gauge pressure is provided inside the pumping chamber by increasing its volume. The negative gauge pressure may, for example, be generated by partially retracting the piston and/or the hollow cylindrical part, depending on which of these parts is movable, from the respective other part. The energy for this action is preferably delivered by the aforementioned means for the temporary storage of mechanical energy.

Due to said increase of volume and said negative gauge pressure, the pumping chamber is filled with liquid or, more specifically, the medically active liquid from the reservoir to which it is fluidically connected. Preferably, a collapsible bag can house the liquid such that advancing emptying of the reservoir will not result in an increasing counter pressure inside the reservoir.

In a subsequent emission phase, a positive gauge pressure is provided inside the pressure chamber. It is recalled that the pressure chamber has said second cross section which is larger than the first cross section of the pumping chamber/piston. As a result, the aforementioned wall/plunger is exposed to said positive pressure.

The positive gauge pressure effects a propulsive movement of the plunger. The higher the pressure is, and the larger the second cross sectional area is, the higher is the force which acts onto the plunger.

Due to the mechanical coupling of plunger and pumping unit, said movement is mechanically transferred or translated to the piston or to the cylindrical part, depending on which one is moveable, such that the volume of the pumping chamber is reduced. It is recalled that the pumping chamber has the interior space of said first cross section. As a result, a positive pressure is generated inside the interior space of the pumping chamber.

Due to the increase in pressure of the pumping chamber, the medically active liquid is emitted from the pumping chamber through the nozzle, where the liquid is atomized.

Due to the ratio of the pressure chamber's second cross section to the interior space's first cross section of the pumping chamber being greater than 1, the pressure of the pressure chamber is amplified with respect to the pressure of the pumping chamber according to said ratio. As a result, a high delivery rate of nebulized liquid and/or a prolonged duration of aerosol emission per actuation of the device (or per pumping cycle) may be achieved. In particular, a high amount of liquid can nevertheless be atomized within a sufficiently short period of time, e.g. an amount of about 50 μl in 1 to 3 seconds.

In one embodiment, the pressure within the pressure chamber is provided by opening a valve to a container with a pressurized gas.

Thus, according to one embodiment, the pressure within the pressure chamber is kept relatively constant during the emission phase. As a result, the pressure which is amplified and transferred to the pumping chamber is constant as well, resulting in a more constant volume flow of nebulized liquid from the nozzle.

According to another embodiment, only at the beginning of the emission phase, a short pulse of pressurized gas is released into the pressure chamber, such that the pressure decreases as its volume increases.

In yet another embodiment, the pressure within the pressure chamber is provided by manually pressurizing said pressure chamber. As a result, the pressure is built up before the emission phase starts. Then also, during the emission phase, the pressure decreases as its volume increases.

According to a preferred embodiment, subsequent to the emission of liquid from the pumping chamber due to the reduction of its volume, the aforesaid means for temporary storage of mechanical energy which has been loaded during the emission phase releases the stored energy. By releasing said temporarily stored energy, the pumping chamber's interior space is increased again. This, in turn, results in a generation of a negative gauge pressure therein, thereby refilling the pumping chamber with liquid from the reservoir.

In another embodiment, the energy necessary for "resetting" the volume of the pumping chamber is provided manually, i.e. by manually pushing the respective parts to the reset position.

During said pumping chamber volume "resetting", also, the volume of the pressure chamber is reset to its initial (minimum) value. At the same time, the pressurized gas should be discharged from said chamber such that said volume reduction is achievable with minimum effort; i.e. it does not become necessary to work against the high pressure to further compress the already pressurised gas. Therefore, in one embodiment, at the beginning of the refilling phase, or between the emission and refilling phase, the pressure chamber's content is discharged from the device into the external environment.

A valve can preferably be used for this purpose. It can be opened and closed automatically as well as manually.

In a third aspect, the present invention relates to the use of the inhalation device according to the first aspect of the invention for the inhalative administration of a medically active liquid in aerosolized form to an animal or human, preferably to a human.

In a fourth aspect, the present invention relates to a method for the treatment, stabilization or prevention of a pulmonary disease or condition (e.g. asthma or chronic obstructive pulmonary disease (COPD)) by inhalative administration of a medically active liquid, wherein the medically active liquid is generated and administered by an inhalation device according to the first aspect of the invention.

It should be noted that with regard to these aspects also, all embodiments, preferred embodiments and combinations thereof as described above in connection with the first and/or the second aspect of the invention apply correspondingly.

DESCRIPTION OF FIGURES

In the following, the invention is described with the aid of accompanying figures. Herein.

All drawings are not to scale and contain only a selection of components, and are presented only in the level of detail which is sufficient to explain the invention. It is clear that for a functioning sample, additional components are necessary which, however, are known to the artisan and omitted here for the sake of conciseness.

Figure 1:
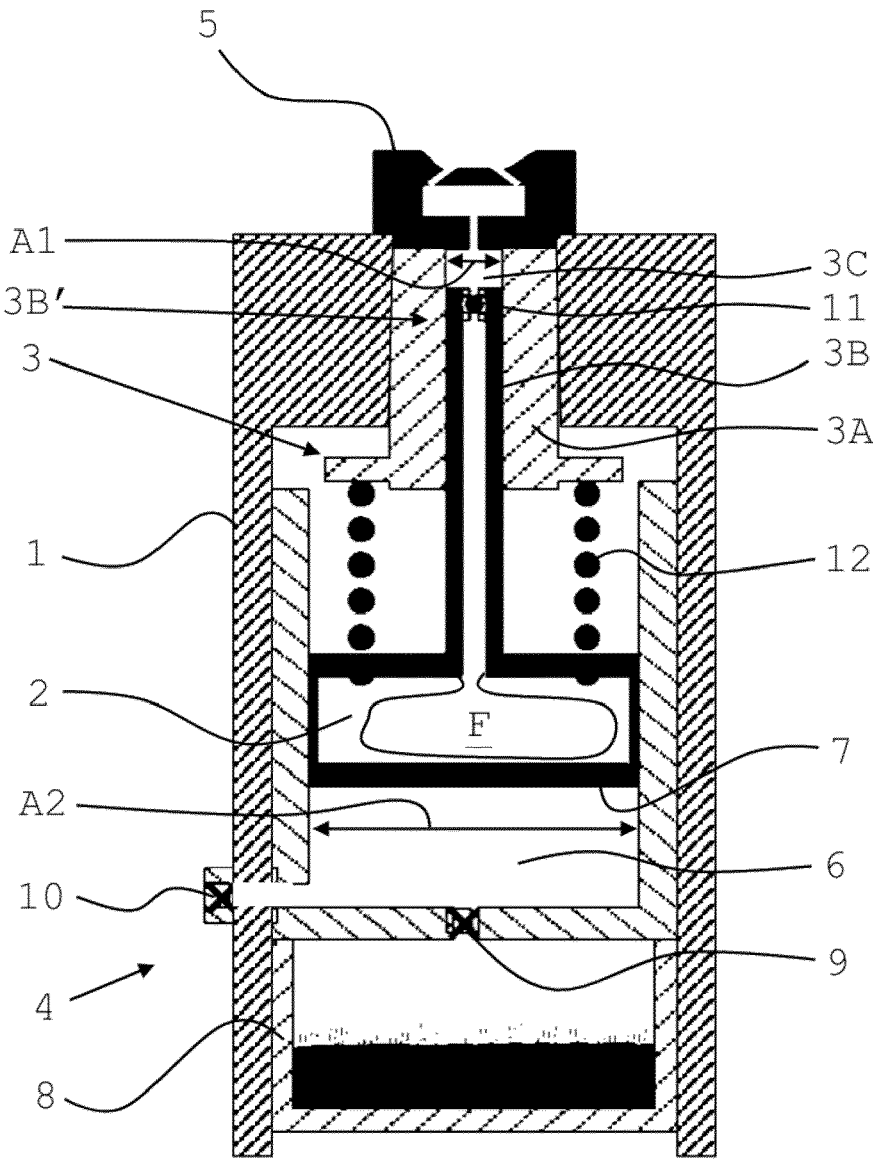
FIG. 1 shows a schematic drawing of some components of one embodiment of an inhalation device.

In FIG. 1, a schematic drawing of some components of one embodiment of an inhalation device is shown.

Depicted are components of an inhalation device which serves for generation of an aerosol. Inside a housing 1, a reservoir 2 is arranged for storing a liquid F. The depicted reservoir 2 contains a collapsible bag which in turn contains liquid F (liquid not depicted). Downstream reservoir 2, a pumping unit 3 is arranged. The pumping unit 3 is connected to a means for the delivery of mechanical energy 4 which feeds said energy to the pumping unit 3.

Downstream of said pumping unit 3, a nozzle 5 is arranged. In the depicted example, the nozzle 5 is of the impingement type.

As can be seen, the pumping unit 3 comprises a hollow cylindrical part 3A and a (in this case) hollow piston 3B. Hollow cylindrical part 3A is immobile and firmly attached to housing 1, and piston 3B is moveable relative to housing 1. In the depicted embodiment, plunger 7 and piston 3B are moveable in parallel, and in fact along collinear, directions.

The cylindrical part 3A has an interior space 3C with a defined first cross section A1. The cross section A1 can have any shape, but is preferably circular. The interior space 3C is configured to receive an upstream end portion 3B' of said piston 3B. In case that the interior space 3C is wider, only that portion of the space 3C is taken in account which in fact serves for receiving piston 3B. Cylindrical part 3A and piston 3B are linearly moveable relative to one another such as to form a pumping chamber. Due to the possibility of said linear movement, the pumping chamber has a variable volume.

According to the invention, the means for the delivery of mechanical energy 4 is a pressurised gas, as described above. The inhalation device comprises a pressure chamber 6 having an internal volume for holding said pressurized gas. A wall of said pressure chamber 6 is provided by a plunger 7. Said plunger 7 is configured to perform a reciprocating linear movement (up- and downwards in the figure). The internal volume of the pressure chamber 6 is related to the position of the plunger, which is in turn dependent on the pressure inside the pressure chamber. An increase of pressure results in a propulsive movement (here, upwards), and a decrease of pressure in a retropulsive movement (here, downwards).

Plunger 7 is mechanically coupled to piston 3B; in a non-depicted embodiment, it can instead or additionally be coupled to cylindrical part 3A. As can be seen, plunger 7 exhibits a cross section A2 which is larger than cross section A1 of the pumping chamber. As a result, an amplification of pressure is achieved, i.e. the pressure in the pumping chamber is higher than in the pressure chamber 6 by an amplification factor or ratio, which is determined by the ratio of cross section A2 to A1.

In the depicted embodiment, the pressurised gas is provided by a container 8 comprising liquefied gas. Part of the gas is present in gaseous form (above level of liquid part, drawn in black). A valve 9 separates container 8 from pressure chamber 6.

A further valve 10 is arranged in a discharge duct of pressure chamber 6. A check valve 11 is arranged upstream the pumping chamber in order to block possible backflow of liquid in direction of the reservoir 2.

A means for the temporary storage of mechanical energy 12, in this embodiment realized by an elastic spring, is provided which is loadable by a propulsive (here, upward) movement of plunger 7. Means 12 is arranged and configured to effect, by unloading its stored energy, a retropulsive (here, downward) movement of the plunger 7 which will be shown below.

In this and the following figures, like reference numerals are used for like parts. In the following figures, some of the references are omitted for the sake of clarity. Also, further on, housing 1 is not shown.

Figures 2, 3, 4:
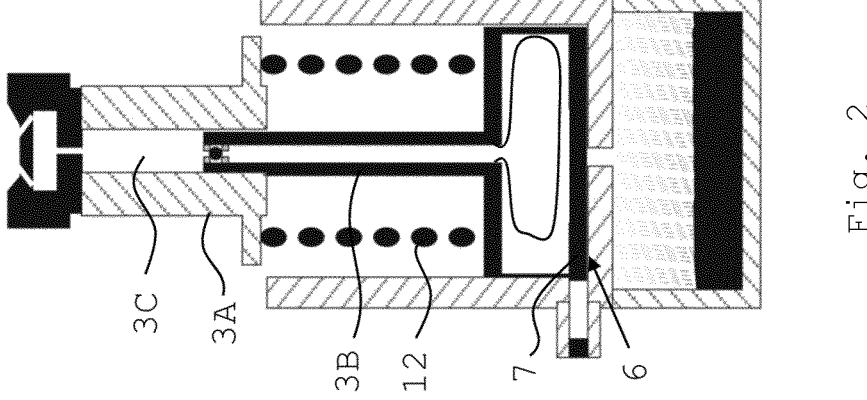
FIG. 2 shows the device of FIG. 1 at the end of the filling phase.
FIG. 3 shows the device of FIG. 1 during the emission phase.
FIG. 4 shows the device of FIG. 1 during the refilling phase.

FIG. 2 shows the situation at the end of the filling phase, with pumping chamber and pressure chamber volumes reset. Interior space 3C of pumping chamber is at a maximum, since piston 3B is at its maximally retracted position with respect to cylindrical part 3A. Plunger 7 is at its lowermost position, so that the volume of pressure chamber 6 is very small, or almost zero. The means for the temporary storage of mechanical energy 12 is relaxed and ready to be loaded with mechanical energy.

In FIG. 3, the emission phase is shown. Valve 9 is now open, such that pressurised gas can flow from container 8 into pressure chamber 6. Plunger 7 moves in direction of arrow 13 (here, upwards), transferring the force acting on the same to piston 3B. Liquid contained in the pumping chamber is therefore emitted through nozzle 5 under high pressure. Arrows 14 indicate two impinging liquid beams that result in the desired nebulization. Means 12 is being compressed, thus temporarily storing mechanical energy.

FIG. 4 shows the situation in the refilling phase. Now, valve 10 is open, such that the pressurized gas can be discharged from pressure chamber 6. No fresh gas can flow into said chamber 6, since valve 9 is now closed. A negative gauge pressure forms inside the pumping chamber which results in refilling the same from reservoir 2. The flow direction is indicated by arrow 15.

The retropulsive movement of the plunger, indicated by arrow 13, is driven by the means for the temporary storage of mechanical energy 12 which now releases its energy to the pumping unit 3, and more precisely, to plunger 7 which is connected with piston 3B. Due to check valve 11, a backflow of liquid from the outside into hollow piston 3B is prevented.

The movement of plunger 7 will come to an end when being in the reset position which is depicted in FIG. 2. The cycle is then complete and another cycle can start from the beginning.

LIST OF REFERENCE NUMBERS 1 housing
2 reservoir
3 pumping unit
3A hollow cylindrical part
3B piston
3C interior space
4 means for the delivery of mechanical energy
5 nozzle
6 pressure chamber
7 plunger
8 container
9,10 valve
11 check valve
12 means for the temporary storage of mechanical energy
13, 14, 15 arrow
A1 first cross section
A2 second cross section
F liquid The following list of numbered items are embodiments comprised by the present invention:

1. Inhalation device for generation of an aerosol of a medically active liquid, comprising: a housing (1), inside this housing (1) a reservoir (2) for storing said medically active liquid, downstream this reservoir (2) a pumping unit (3) for generation of a pressure connected to a means for the delivery of mechanical energy (4) to said pumping unit (3), and downstream said pumping unit (3) a nozzle (5);
   wherein the pumping unit (3) comprises a hollow cylindrical part (3A) and a piston (3B), the cylindrical part (3A) having an interior space (3C) with a defined first cross section (A1) configured to receive an upstream end portion (3B') of said piston (3B), wherein said cylindrical part (3A) and said piston (3B) are linearly moveable relative to one another such as to form a pumping chamber having a variable volume,
   characterized in that
   the means for the delivery of mechanical energy (4) is a pressurised gas, wherein the inhalation device comprises a pressure chamber (6) having an internal volume for holding said pressurized gas, a wall of said pressure chamber (6) being provided by a plunger (7) which is configured to perform a reciprocating linear movement such as to change the internal volume of the pressure chamber (6), wherein the plunger (7) is mechanically coupled to the piston (3B) or to the cylindrical part (3A), and wherein the plunger (7) exhibits a cross section (A2) which is larger than the cross section (A1) of the pumping chamber.

2. Inhalation device according to item 1, wherein the ratio is greater than 10.

3. Inhalation device according to item 1 or 2, wherein the pressurised gas is provided by
   a container (8) filled with pressurized and/or liquefied gas, or
   a chamber which is manually pressurizable, and which can temporarily hold and controllably release said pressurised gas.

4. Inhalation device according to any of items 1 to 3, wherein the piston (3B) is hollow.

5. Inhalation device according to any of the preceding items, wherein either,
   the piston (3B) is immobile and firmly attached to the housing (1) or to the nozzle (5), and the hollow cylindrical part (3A) is moveable relative to the housing (1) or to the nozzle (5), or
   the hollow cylindrical part (3A) is immobile and firmly attached to the housing (1) or to the nozzle (5), and the piston (3B) is moveable relative to the housing (1) or to the nozzle (5).

6. Inhalation device according to any of the preceding items, wherein a check valve (11) is arranged upstream the pumping chamber in order to block backflow of liquid in direction of the reservoir (2).

7. Inhalation device according to any of the preceding items, wherein additionally, a mechanical lever mechanism is provided for further increasing the aforesaid ratio.

8. Inhalation device according to any of the preceding items, wherein a means for the temporary storage of mechanical energy (12) is provided which is loadable by a propulsive movement of the plunger (7), and which is configured, by unloading its stored energy, to effect a retropulsive movement of the plunger (7).

9. Inhalation device according to item 8, wherein said means for the temporary storage of mechanical energy (12) is an elastic spring, a gas spring, or a magnetic spring.

10. Inhalation device according to any of the preceding items, wherein the nozzle (5) is of the impingement type, and/or wherein the volume of the pumping chamber amounts to at least 30 µl, or at least 50 µl, or from about 100 to 250 µl, respectively, and wherein the pumping unit (3) is configured to provide a pressure of at least 100 bar inside the pumping chamber.

11. Inhalation device according to any of the preceding items, wherein (i) the plunger (7) and (ii) the piston (3B) and/or the cylindrical part (3A) are moveable in parallel directions.

12. Method for generation of an aerosol of a liquid by means of an inhalation device as defined in item 1, wherein the method comprises the following steps:

in a filling phase, providing a negative gauge pressure inside the pumping chamber by increasing its volume, and thereby filling the pumping chamber with liquid from the reservoir (2) due to said negative gauge pressure;

in an emission phase, providing a positive gauge pressure inside the pressure chamber (6) having said second cross section (A2), and thereby effecting a movement of the plunger (7);

transferring said movement mechanically to the piston (3B) or to the cylindrical part (3A), such that the volume of the pumping chamber is reduced, and a positive pressure is generated inside its interior space; and thus emitting the medically active liquid from the pumping chamber through the nozzle (5);

wherein the pressure of the pressure chamber (6) is amplified.

13. Method according to item 11, wherein the pressure within the pressure chamber (6) is provided by opening a valve (9) to a container (8) with a pressurized gas, or by manually pressurizing said pressure chamber (6).

14. Method according to item 12 or 13, wherein, subsequent to the emission of liquid from the pumping chamber due to the reduction of its volume, a means for temporary storage of mechanical energy (12) which has been loaded during the emission phase releases the stored energy, thus increasing the pumping chamber's interior space again, resulting in a generation of a negative pressure therein, thus refilling the pumping chamber with medically active liquid from the reservoir (2).

15. Method according to any of items 12 to 14, wherein, at the beginning of the refilling phase, the pressure chamber's (6) content is discharged to the atmosphere.

What is claimed is:

1. An inhalation device for generation of an aerosol of a medically active liquid, the inhalation device comprising:

a housing comprising therein:

a reservoir configured to store the medically active liquid;

a pumping unit located downstream from the reservoir;

a nozzle located downstream from the pumping unit;

the pumping unit comprising a hollow cylindrical part and a piston, the hollow cylindrical part having an interior space with a defined cross section configured to receive an end portion of the piston, wherein the hollow cylindrical part and the piston are linearly moveable relative to one another forming a pumping chamber with a variable volume;

a plunger mechanically coupled to the piston or to the hollow cylindrical part of the pumping unit and having a cross section larger than the cross section of the hollow cylindrical part, the plunger configured to translate in a reciprocating linear movement within the housing; and a pressure chamber having a variable internal volume defined by the housing and a position of the plunger in the housing, the pressure chamber configured to receive a pressurized gas, wherein the pressure chamber comprises an inlet valve and an outlet valve with separate ports into the pressure chamber, and the pressurized gas is configured to exert a force on and translate the plunger within the housing increasing the variable internal volume of the pressure chamber and delivering mechanical energy to the pumping unit to decrease the variable volume of the pumping chamber and generate the aerosol of the medically active liquid.

2. The inhalation device according to claim 1, wherein a ratio of the cross section of the plunger to the cross section of the hollow cylindrical part is greater than 2.

3. The inhalation device according to claim 2, wherein the ratio of the cross section of the plunger to the cross section of the hollow cylindrical part is greater than 10.

4. The inhalation device according to claim 1, wherein the pressurized gas is provided by:

a container filled with pressurized or liquefied gas, or a chamber configured to temporarily hold and controllably release said pressurized gas.

5. The inhalation device according to claim 1, wherein the piston is hollow.

6. The inhalation device according to claim 1, wherein a check valve is arranged upstream of the pumping unit in order to block backflow of liquid in the direction of the reservoir.

7. The inhalation device according to claim 1, wherein a spring is provided, which is configured to be loaded by a propulsive movement of the plunger, and which is configured, by unloading its stored energy, to effect a retropulsive movement of the plunger.

8. The inhalation device according to claim 7, wherein the spring is an elastic spring, a gas spring, or a magnetic spring.

9. The inhalation device according to claim 1, wherein the nozzle is an impingement nozzle.

10. The inhalation device according to claim 1, wherein the variable volume of the pumping chamber ranges from a maximum of about 100 to 500 µl.

11. The inhalation device according to claim 1, wherein the pumping unit via the pressure chamber is configured to provide a pressure of at least 100 bar inside the pumping chamber.

12. The inhalation device according to claim 1, wherein (i) the plunger; and (ii) the piston or the hollow cylindrical part are moveable in a direction parallel to a vertical plane.

13. A method for generating an aerosol of a liquid by means of an inhalation device as defined in claim 1, wherein the method comprises the following steps:

providing, in a filling phase, a negative gauge pressure inside the pumping chamber by increasing its volume, thereby filling the pumping chamber with liquid from the reservoir due to said negative gauge pressure;

providing, in an emission phase, a positive gauge pressure inside the pressure chamber having said second cross section, thereby effecting a movement of the plunger;

transferring said movement mechanically to the piston or to the cylindrical part, such that the volume of the pumping chamber is reduced, and a positive pressure is generated inside its interior space; and emitting the medically active liquid from the pumping chamber through the nozzle.

14. The method according to claim 13, wherein the positive gauge pressure within the pressure chamber is provided by opening a valve to a container with a pressurized gas, or by manually pressurizing said pressure chamber.

15. The method according to claim 13, wherein, subsequent to the emission of liquid from the pumping chamber due to the reduction of its volume, the method further comprises releasing stored energy from a temporary storage of mechanical energy which has been loaded during the emission phase thus increasing the pumping chamber's interior volume again, resulting in a generation of the negative pressure therein, thus refilling the pumping chamber with medically active liquid from the reservoir.

16. The method according to claim 13, wherein, at the beginning of the refilling phase, discharging the pressure chamber's content to the atmosphere.

17. A method of inhalatively administering a medically active liquid to an animal or human, the method comprising inhalatively administering the medically active liquid in aerosolized form with the inhalation device of claim 1 to the animal or human.

18. A method for the treatment, stabilization or prevention of a pulmonary disease or condition by inhalative administration of a medically active liquid, comprising generating and administering the medically active liquid using an inhalation device according to claim 1.

\*   \*   \*   \*   \*